United States Patent [19]

Hansen et al.

[11] Patent Number: 5,714,225
[45] Date of Patent: Feb. 3, 1998

[54] SKIN PLATE PRODUCT

[75] Inventors: Henrik Christian Hansen, Copenhagen NV; Tarras Wanheim, Frederiksberg, both of Denmark

[73] Assignee: Coloplast A/S, Humlebak, Denmark

[21] Appl. No.: 614,944

[22] Filed: Mar. 11, 1996

Related U.S. Application Data

[63] Continuation of Ser. No. 182,763, Jan. 14, 1994, abandoned.

[30] Foreign Application Priority Data

Jan. 15, 1993 [DK] Denmark ................. 0048/93

[51] Int. Cl.$^6$ .............. A61F 13/02; A61L 15/44; A61L 15/58
[52] U.S. Cl. ............. 428/114; 428/37; 428/64.1; 428/107; 428/195; 428/343; 428/349; 428/351; 428/355; 424/443; 424/447; 424/448; 602/48; 602/55; 604/307; 604/336; 604/308; 604/304
[58] Field of Search ............ 428/37, 64.1, 107, 428/114, 195, 343, 349, 351, 355; 424/443, 447, 448; 602/55, 48; 604/307, 336, 308, 304

[56] References Cited

U.S. PATENT DOCUMENTS

| 3,339,546 | 9/1967 | Chen . |
| 3,419,006 | 12/1968 | King et al. . |
| 3,645,835 | 2/1972 | Hodgson . |
| 3,972,328 | 8/1976 | Chen . |
| 4,093,673 | 6/1978 | Chang et al. . |
| 4,231,369 | 11/1980 | Sorensen et al. . |
| 4,699,792 | 10/1987 | Nick et al. ........................ 424/446 |
| 4,728,642 | 3/1988 | Pawelchak et al. . |
| 4,793,337 | 12/1988 | Freeman et al. . |
| 4,867,748 | 9/1989 | Samuelsen . |
| 5,051,259 | 9/1991 | Olsen et al. . |

FOREIGN PATENT DOCUMENTS

| 415183 | 3/1991 | European Pat. Off. . |
| 272149 | 3/1992 | European Pat. Off. . |
| 243069 | 11/1992 | European Pat. Off. . |
| 170010 | 6/1985 | Germany . |
| 1280631 | 7/1972 | United Kingdom . |
| 8806894 | 3/1988 | WIPO . |

*Primary Examiner*—Kathleen Choi
*Attorney, Agent, or Firm*—Ostrolenk, Faber, Gerb & Soffen, LLP

[57] ABSTRACT

The skin plate product according to the invention is an adhesive, flat skin plate product for use as a semi-manufacture in the production of dressings, skin and wound care devices, fastening means for dressings, ostomy equipment, wound drains and catheters for incontinence equipment, in particular for men, and for use in electrodes for application to the skin, the said skin plate product having an area being delimited by the periphery of the product, and a first surface and a second surface consisting of two or more essentially non-mixed material units (1, 1', 2, 2', 2a, 2b, 2c, 4, 11, 12, 21, 21', 22, 22', 31, 32, 33, 41, 42, 43), at least two material units being of different material, of which at least one material unit is a skin friendly self-adhesive material, and where a first material unit (1, 1', 11, 21, 21', 31, 41) extends throughout the area of the entire product, this material unit further constituting at least a portion of the first surface (6, 26, 26', 36, 46) and the second surface (5, 25, 25', 35, 45), respectively, and the additional material unit or units constituting the other portion of the first and the second surface, respectively, and having a thickness which extends at least somewhat into the thickness of the product in a direction which intersects the first or second surface of the product.

20 Claims, 5 Drawing Sheets

SKIN PLATE PRODUCT

This is a Continuation of application Ser. No. 08/182,763 filed on Jan. 14, 1994, now abandoned.

BACKGROUND OF THE INVENTION

The present invention relates to an adhesive, flat skin plate product for use as a semi-manufactured product in the production of dressings, skin- and wound-care devices, fastening means for dressings, ostomy equipment, breast prostheses, wound drains and catheters for incontinence equipment, in particular for men, and for use in electrodes for application to the skin, and a method of producing such a skin plate product.

A variety of skin plate products of this type is known which consist of or comprise a skin friendly adhesive material which may e.g. comprise a continuous phase containing an adhesive and e.g. being built from an elastomer, a plasticizer for the elastomer, an adhesion promoting resin and optionally an oil-based extender as well as an antioxidant. In this product, there is often a discontinuous phase comprising one or more water-soluble or water-swellable hydrocolloids, starch derivatives or cellulose derivatives or hydrophilic polymers, and optionally one or more medicaments.

DK patent No. 157 899 discloses a flat skin plate product of the kind described above, which consists of alternating material units of at least two different kinds, at least one of which is a skin friendly self-adhesive material. The material units are essentially parallel and extend throughout the product in a direction which intersects the main surfaces of the product, preferably perpendicularly. The material unit may e.g. be parallel or coaxial layers, so that the product has the nature of a laminate, the individual layers of which are quite short. They may also be short strands.

This known skin plate product offers the advantage that it may be produced to comprise, besides the adhesive material itself, other components for special purposes, e.g. containing antiseptics, medicaments or other biologically active substances or liquid-conducting or electrically conductive structures.

The skin plate product known from DK patent specification No. 157 899 is produced by coextruding the various material units or by rolling up layers of the various material units positioned on top of each other so as to form a long cylindrical mass which is subsequently cut into thin slices.

It has turned out in practice to be very cumbersome and costly to produce the product, since the handling of the incorporated adhesive mass and the cutting step place heavy demands on the machinery used, and at the same time it is necessary that the cutting station is kept completely free of adhesive residues. As a consequence, it is often necessary to stop the production to clean the cutting station. At the same time, there is a rather large waste, since the thin adhesive slices easily crumble during cutting.

All in all, these production difficulties contribute to making the product considerably more expensive.

The skin barrier product known from DK patent No. 157 899 has the good characteristic that it is possible to vary the properties in the surface direction, which offers a high degree of liberty when constructing the product. The various alternating material units can e.g. consist of materials with different adhesive properties, just as one or more of the material units may be non-adhesive. The material units may further have more or less pronounced barrier properties, be liquid-conducting or electrically conductive to various degrees or contain wound-healing substances, medicaments or absorbing materials.

It appears from DK patent No. 157 899 that the alternating material layers may further form an angle with the surfaces of the skin plate product. However, in practice such products are very difficult to produce economically.

The skin plate product known from DK patent No. 157 899 thus has the less desirable property that both surfaces of the skin plate necessarily exhibit the same material configuration. This is not always expedient, since the two surfaces are to adhere to different materials, (i) one of them to the skin, and (ii) the other to e.g. a backing layer, an ostomy flange or other device.

It is the object of the present invention to devise a skin plate product of the kind stated above and essentially having the same good properties as the skin plate product patented in DK patent No. 157 899, and at the same time being significantly cheaper to produce.

It is a further object of the present invention to devise a skin plate product of the kind stated above which essentially has the same good properties as the skin plate product patented in DK patent No. 157 899, and where the two surfaces of the skin plate product may be different.

DESCRIPTION OF THE INVENTION

The skin plate product may consist of two or more different materials, at least one of the materials being a skin friendly adhesive.

The skin friendly adhesive may be of any kind, e.g. an acrylic adhesive, a hydrogel adhesive or a hydrocolloid adhesive. The adhesive material may e.g. comprise caoutchouc, caoutchouc-like synthetic homo-, co- or block-copolymers, polyacrylate and copolymerisates thereof, polyurethane, silicone, polyisobutylene, polyvinyl ether and natural or synthetic resins or mixtures thereof optionally containing zinc oxide. The adhesive matrix may further contain various additives, such as plasticizers, thickeners and others, and optionally hydrocolloids and/or various medicaments, such as antiseptics, hormones, nicotine, etc.

Skin friendly adhesives include e.g. those which are mentioned in GB patent specification No. 1 280 631, in DK patent specifications No. 127 578, No. 148 408, No. 154 806, No. 147 226 and No. 154 747, in EP published specifications No. 97 846 and No. 415 183, in SE published application No. 365 410, in WO published specification No. 88/6894, in U.S. Pat. Nos. 339,546, 4,093,673 and 4,867, 748, and in NO published application No. 157 686.

A further example of a usable adhesive material is the one known from U.S. Pat. Nos. 4,231,369 and 4,367,632. The adhesive materials herein disclosed comprise (I) a continuous phase comprising (a) a physically cross-linked elastomer in the form of one or more styrene-isoprene-styrene block copolymers or ethylene-propylene block copolymers, (b) a hydrocarbon resin in the form of a polymer or copolymer of cyclopentadiene, dicyclopentadiene, α-pinene and/or β-pinene, (c) an antioxidant, (d) optionally an oil-extender consisting of one or more mineral oils, and (e) optionally a plasticizer which is polar to the elastomer, e.g. an ester of a polyethylene glycol or polypropylene glycol, or an ester of a di- or polybasic carboxylic acid with a preferably aliphatic alcohol, and (II) a phase dispersed in the continuous phase comprising one or more water-swellable hydrocolloids.

A particularly preferred adhesive is disclosed in U.S. Pat. No. 3,339,546, including in particular an adhesive comprising polyisobutylene and one or more hydrocolloids being swellable in aqueous liquid.

Furthermore one or more of the units, provided they do not get into contact with the skin in use, may consist of a non-skin friendly adhesive material.

According to the invention, at least one of the material units may consist of a material hampering or preventing substance migration to and from the self-adhesive or non-self-adhesive material units being in contact with these material units. In other words, it is a case of more or less effectively acting barrier-forming material units.

These barrier-forming material units may be of several different types, i.e. they may have different barrier effects against substances of the same kind or have barrier effects against different substances.

This embodiment is particularly significant in situations where the units of the self-adhesive adhesive are in contact with units of another kind, and it is desired to prevent substance migration from within or out into these units of another kind. At least one of the kinds of the material units may consist of a material hampering or preventing migration of aqueous liquids to neighboring hydrocolloid-containing self-adhesive materials.

By a substance migration hampering material is meant a material where e.g. liquid migrates more slowly than in a neighboring material.

According to the invention, the substance migration hampering or preventing units may consist wholly or partly of film or foil of plastic or metal. Such barrier foils or films will most often be perforated or in the form of a netting and have a thickness of 10–100 μm, and consist e.g. of polyolefins, polyesters, polyvinylchloride, aluminum or laminates thereof. Such a barrier foil or film will, however, for reasons of production most often be placed in contact with another additional unit, these units together preferably having a thickness exceeding 0.1 mm.

The substance migration hampering or preventing material units may further according to the invention consist of a material which is ductile under the influence of low force impacts and also is more or less hydrophobic and containing a self-adhesive elastomer mass and hydrocolloid, optionally in another amount or of a different type than in the neighboring material unit or units.

From DK patent specification No. 157 899 it is known to select the alternating layers so that at least one layer consists of a liquid migration hampering or preventing material. By the therein described skin plate product with liquid migration hampering or preventing layers, when used in ostomy equipment or a dressing for exudating wounds, is achieved a somewhat prolongs wearlife of the adhesive surface facing the skin, since the substance migration hampering or preventing layers hamper the migration of liquid in the surface direction of the skin plate product.

The skin plate product according to the invention may also be produced so as to hamper migration of liquid in the surface direction of the skin plate product.

Particular preference is given to a skin plate product consisting of two or more mutually contacted material units, each comprising a skin friendly adhesive containing hydrocolloid, but with different cohesion properties.

Such a skin plate product may e.g. consist of a first material unit of a skin friendly adhesive having a relatively high cohesion and containing hydrocolloid as well as one or more additional material units, at least one of which is a skin friendly adhesive having a relatively low cohesion and additionally containing hydrocolloid.

In an alternative embodiment of the invention, the skin plate product consists of a first material unit of a skin friendly adhesive having a relatively low cohesion and containing hydrocolloid, as well as one or more additional material units, at least one of which is skin friendly adhesive having a relatively high cohesion and additionally containing hydrocolloid.

It has thus been found that the liquid migration speed in a hydrocolloid-containing adhesive is dependent on the cohesion of the adhesive, i.e. the lower cohesion, the faster liquid migration, and vice versa.

The liquid migration speed also depends on the amount and type of hydrocolloid present in the skin plate product, so that the liquid migration speed increases with increasing content and increasing absorbing capacity of the hydrocolloid.

It is, however, essential that the total liquid absorbing capacity of the skin plate product is high, since the wearlife of the skin plate product is very dependent on this capacity.

Suitable adhesives for this preferred skin plate product in particular include the adhesives described in U.S. Pat. No. 3,339,546, and in particular adhesives containing a binder consisting of polyisobutylene and optionally a rubber, in particular butyl rubber, and hydrocolloid, optionally in the form of a mixture of different hydrocolloid materials, such as gelatin, pectin, guar and sodium carboxymethylcellulose. Adhesives of this type may constitute both the more cohesive first material unit and one or more less cohesive additional material units.

The cohesion in such adhesives may be varied by changing the molecular weight of the polyisobutylene, or by adding or increasing the content of a further binder in the form of another elastomer having a higher molecular weight.

In a particularly preferred embodiment the first material unit consists of a cohesive adhesive composed of low molecular weight polyisobutylene, such as the one sold by EXXON under the tradename "Vistanex LH-MH" (average mole weight Mw=82.000 g/mol), butyl rubber, such as the one sold by EXXON under the tradename "Butyl 007" (Mw=420.000 g/mol), and hydrocolloid, e.g. in the form of an essentially equal mixture of gelatin, pectin and sodium carboxymethylcellulose. The total hydrocolloid content is preferably 30–70%, in particular about 50%. Further, one or more of the additional units consist(s) of a less cohesive adhesive composed of low molecular polyisobutylene, e.g. "Vistanex LM-MH" and 30–70% hydrocolloid, in particular about 60%, in the form of an essentially equal mixture of gelatin, pectin and sodium carboxymethylcellulose.

The ratio between the amount of polyisobutylene and butyl rubber in the first material unit depends on how cohesive and consequently how liquid migration hampering the material is desired to be. The higher the butyl rubber content, the more cohesive the material. The less cohesive material which constitutes one or more additional units may further also contain a minor amount of butyl rubber.

Alternatively, the cohesive first material unit may consist of an adhesive such as the one which is mentioned in DK patent specification No. 147 034 (corresponding to U.S. Pat. No. 4,231,369) and which has been described above.

A skin plate product according to the invention may e.g. consist of a first cohesive adhesive material unit and one or more additional material units of a less cohesive adhesive material. The adhesive materials may have the following compositions in terms of weight-%.

|  | Less cohesive adhesive | Cohesive adhesive |
| --- | --- | --- |
| Polyisobutylene (PIB) | 40–60 | — |
| Styrene isoprene styrene (SIS) |  | 5–20 |
| Oil |  | 5–30 |
| Resin |  | 10–30 |
| Sodium carboxymethylcellulose (CMC) | 25–40 | 25–40 |
| Guar | 10–25 | 10–25 |

PIB may e.g. be the above-mentioned "Vistanex LM-MH".

SIS may e.g. be "Cariflex TR 1107" which is sold by SHELL.

The oil may e.g. be a liquid paraffin.

The resin may e.g. be a fully hydrogenated synthetic thermoplastic resin, such as "Arkon 90", which is sold by Arakawa (Japan).

The cohesion of an adhesive is measurable empirically e.g. by measuring how fast or to which degree the material disintegrates upon contact with excess liquid. The faster or the higher degree of disintegration, the less cohesive the material.

By a skin plate product having this preferred embodiment, i.e. with a first very cohesive self-adhesive material unit and at least one additional less cohesive self-adhesive material unit, or by a variation thereof where the first material unit is of a less cohesive self-adhesive material than one or more cohesive self-adhesive additional material units, the following advantageous properties of use are simultaneously obtained:

A quick initial absorption of liquid from the skin surface is achieved, which results in an improved initial adhesion. The less cohesive adhesive will very quickly conduct the liquid away from the skin and into the skin plate product.

A continuing good adhesive capacity is obtained, since the less cohesive adhesive layer is correspondingly plastic and will form itself so as to follow the uneven contour of the skin surface.

A skin plate product with a long wearlife is obtained, since the liquid is slowly, but constantly, conducted from the less cohesive adhesive to the more cohesive material, so that the washing out of the less cohesive adhesive material is significantly reduced in comparison with the washing out in skin plate products consisting of only the less cohesive adhesive material.

A skin plate product is obtained which leaves less adhesive residue upon removal than skin plate products where the adhesive material is only of a less cohesive adhesive material. This also links up with the reduced washing out of the less cohesive adhesive.

A skin plate product is obtainable which in comparison with skin plate products without liquid barrier layer has a reduced tendency to unwanted absorption of liquid from the edges, for instance water from bathing, or secretion from stomas in case of its application for fastening ostomy equipment.

A large number of other materials may be incorporated in the product according to the invention, either as independent units or as portions of adhesive-containing units. An example hereof is that one or more types of material units may consist of a foam material with open or closed cells. The foam material may contain a biologically active substance, e.g. a medicament or an antiseptic or antibiotic. The biologically active substance may be present in the cells of a foam with open cells, or be present in the foam material itself, that is in the walls of open or closed cells which may e.g. consist of a foamed gel material, such as gelatin.

Biologically active substances may also be present in other material than foam materials. E.g. one or more material units may be built from a hydrophilic gel material containing an agent effective against warts, e.g. cantharidine, salicylic acid, silver nitrate, podophyllin or an anti-metabolic cystostatic, such as cytarabine, fluorouracil or mercapto-purine.

One or more material units may be built from a hydrophilic gel material including one or more keratolytically active substances, e.g. carbamide, salicylic acid and/or lactic acid.

Further, one or more material units may contain one or more compounds impeding mitosis, e.g. anthracene, silver nitrate or glucocorticoids, such as mildly, medium strongly or strongly active corticosteroids, such as hydrocortisone, triamcinolon acetonide or betametasone.

One or more of the material units may as mentioned above be gels with adhesive properties, or they may be gels devoid of adhesive properties. Such gel materials may be hydrophilic or hydrophobic, optionally of a desired HLB (hydrophilic-lipophilic balance), and optionally a supporting structure may be incorporated therein in the form of a foam of e.g. polyether, collagen or gelatin, or in the form of fibers, filaments or woven or non-woven textile material, e.g. of polyester or cotton. Hydrophilic gels may e.g. be mixtures of karaya and glycerol; of pectin, comparatively low-molecular polyethylene glycol and glycerol; or mixtures of gelatin, glycerol and water.

Hydrophobic gels may e.g. consist of mixtures of styrene-isoprene-styrene block copolymer and liquid paraffin; mixtures of styrene-isoprene-styrene block copolymer, liquid paraffin and dioctyladipate; or mixtures of nitrocellulose, ricinus oil and rosin.

As examples of active substances which may be incorporated into the gel materials may further be mentioned antiseptics, such as iodophors, silver compounds, hexidine or chlorohexamine, vitamins and antibiotics, wound-healing agents and growth-promoting substances, such as growth hormone.

Foam materials which may be present as a special kind of material unit or form a supporting structure in the gel materials just mentioned, may e.g. be of polyether, polyethylene, polyvinyl chloride, polyurethanes, gelatin or collagen.

One or more of the material units may further consist of or contain alginate, e.g. in the form of a fibrous and/or porous alginate pad, preferably containing a mixture of sodium alginate and calcium alginate. Mention of such alginate materials can e.g. be found in EP patent application No. 243 069 or in SU certificate No. 1 171 476.

The skin plate product may also incorporate one or more material units with so-called superabsorbing materials. These are well-known in connection with absorption products, such as sanitary towels and diapers.

The skin plate product according to the invention may further comprise one or more material units of a hydrophilic, electrically conductive gel material, optionally encased by aluminum foil e.g. consisting of a base polymer, such as polyacrylamide, salts of polymethacrylic and polyacrylic acids, polyvinyl alcohol or Na-CMC, plasticized with a low viscous plasticizer, e.g. a liquid polyol, such as glycerol and optionally with addition of typically 0.1–1.5% NaCl, KCl, or another biologically harmless, readily soluble salt, and if desired 1–10% water.

As mentioned, the skin plate product according to the invention consists of at least two material units of different material, the first material unit constituting at least a portion of the first surface and the second surface, respectively, the first material unit optionally constituting the entire one surface.

The remaining surface area is constituted by the additional material unit or units which extend(s) at least somewhat into the product, so that an axis which is flush with the contact surfaces between the first unit and an additional unit in the zone adjoining the said surface and intersects it is preferably perpendicular thereto, but may also have a slightly oblique angle. The additional material units preferably have a thickness of 0.1–3 mm, in particular 0.5–1.5 mm, and preferably have a thickness less than ¾ of the total thickness of the product, in particular less than ½ of the total thickness of the product.

The thickness of an additional material unit is measured as the distance between the surface adjoining the point on the additional unit which is closest to the opposite surface of the product and the point itself, the measuring axis being perpendicular to the surfaces.

If both surfaces have areas which are constituted by additional material units and which overlap, it is necessary that these material units together have a thickness which does not exceed the thickness of the aggregate product.

The surface area or areas being constituted by one or more additional material units may each have a surface having the shape of an island, preferably having a minimum width of more than 0.5 mm.

If there is only one island, it may suitably have a minimum width of 25–50 mm.

Alternatively, the first and/or second surface of the skin plate product may be constituted by one or more islands of the first material unit, the remaining portion of such a surface being constituted by one or more additional material units.

By island is meant an essentially circular, oval, square or rectangular surface.

The surface area or areas being constituted by additional material units may also be one or more concentric circular or encircling path areas, preferably having a zone width of 0.5–10 mm, in particular 1–5 mm.

If there are two or more concentric path areas of additional material units, the first material unit preferably constitutes a circular or encircling surface area between the concentric path areas of the additional material units having a width of 1–20 mm, and in particular of 1–5 mm, the path areas of the first material unit preferably being 0.3–3 times wider than the path areas of the additional material units.

The surface areas being constituted by the additional material units may naturally have many other embodiments. E.g. they may have the form of one or more strips, curves, triangles, spirals or combinations of these and of the above described embodiments. In view of the production of the product it is, however, expedient that these surface areas have a minimum width of more than 0.5 mm.

The product according to the invention may be circular, oval, square or rectangular or have any other embodiment. For use in ostomy equipment the product according to the invention may e.g. have a central aperture.

The configuration of the material units and the choice of materials of course depend on for which use the skin plate product according to the invention is intended, i.e. which properties it is desired that the product should have, just as the total area and thickness of the product depend on this.

It is, however, preferred that the product according to the invention has a total thickness of less than 4 mm and preferably less than 2 mm.

Further, it is generally preferred that the first material unit is a skin friendly adhesive, and that at least one of the two contacting material units is self-adhesive.

The invention also relates to a method of producing the skin plate product according to the invention, the method being characterized by i) producing from the material which is to constitute the first material unit a flat plate and optionally cutting it into smaller pieces having a periphery corresponding to the desired product periphery; ii) producing the second additional material unit or units with essentially the thicknesses and surfaces which they are intended to have in the finished product; iii) pressing the second material unit or units into the first material unit, and iv) punching or cutting the product to the desired periphery, if this is not done in step i).

The flat plate produced in step 1 is produced in a manner known per se by coating, extrusion or compression.

The thickness of this plate may be varied depending upon how large a portion of the finished product is intended to be constituted of additional material units, and how much post-calibration is acceptable. In practice the thickness will vary from 20–100% of the thickness which the finished product is intended to have.

The flat plate produced may optionally be cut into pieces which essentially have the desired product periphery. It is, however, preferred to postpone the cutting until the additional material units have been incorporated in the plate.

If both surfaces of the product are to have areas which are constituted by additional material units, it is expedient to perform this in two steps, by first pressing in the material units in one surface, and then in the other. Alternatively, it may be performed in 1 step by simultaneously pressing in additional material units in both surfaces.

If only one of the surfaces of the product is to have areas which are constituted by additional material units, the other surface may, if desired, in advance be coated with a secondary adhesive layer, a film material or the like.

The additional material units may e.g. be produced by extruding or cutting/punching plates or laminates, which e.g. may comprise a netting or foil. An additional material unit may furthermore be produced by the production method according to the invention. In a special embodiment of the method according to the invention in which the product comprises one additional unit, this unit may if desired be produced by punching a material plate, so that this additional unit obtains a shape having a periphery corresponding to the periphery of the finished product, at least one throughgoing aperture being punched in this additional unit.

At the moment of pressing in in step iii), some material will be displaced in the flat plate which is to constitute the first unit. The additional material unit or units must be pressed so far into the first material unit that the flat side into which the additional unit or units are to be pressed essentially ends up being plane. If an additional material unit consists of a perforated material plate sufficient material must thus be displaced from the first unit to fill out these apertures.

At the pressing in of the additional unit or units into the flat plate, the additional units may advantageously be harder than the flat plate at the moment of pressing in. This is controllable by cooling in advance the additional material unit or units and/or heating the first material unit.

When large amounts of materials are to be displaced in the first material unit, it is advantageous prior to the pressing in in step iii) to pre-displace the material by depressing recesses in the plate which is to constitute the first material unit.

If first recesses are depressed in the flat plate and subsequently the additional material units are placed in the recesses, it may be expedient nevertheless to exert a light pressure on the additional material units to ensure safe positioning thereof.

Such pre-depressed recesses may expediently be made so as to correspond to the thickness and the desired configuration of the additional material unit or units to be positioned in the recesses.

The optimum pressing in speed depends on the nature of the materials, and in particular on their plastic/elastic properties.

Immediately before or during the final punching of the product according to the invention, it may further be expedient to subject the product to light heating and/or pass it through calibration rollers to ensure that the material units cohere sufficiently and have plane surfaces.

Figure 1:
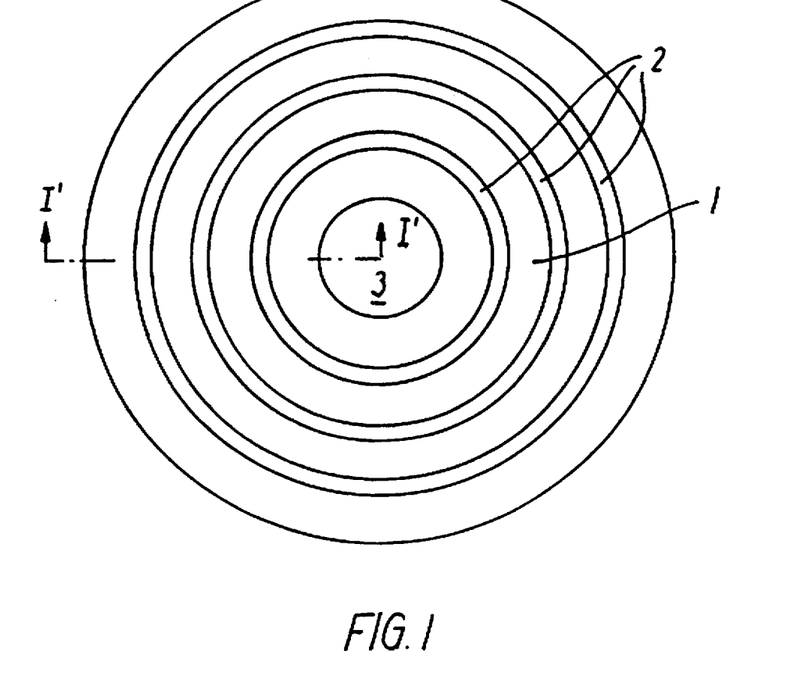
FIG. 1 shows a first embodiment of the skin plate product according to the invention seen from the side intended for a skin surface.

The skin plate product shown in FIG. 1 consists of a first material unit 1 and three additional material units 2. The skin plate product has a first not shown surface and a second surface intended for facing a skin surface.

The second surface is constituted by the first material unit 1 and concentric path areas of the additional three material units 2 which are depressed into the first material unit 1.

In the figure shown, three additional circular path areas of additional material units are drawn, but there may just as well be 1, 2, 4 or more path areas, and they may further have any other encircling construction.

The skin plate product shown is especially suited for use in ostomy equipment, and therefore the product is provided with a central aperture 3.

However, the product may just as well be constructed without this aperture, e.g. for use in a wound dressing.

The first material unit 1 is preferably of a liquid absorbing skin friendly adhesive material having a high cohesion, as mentioned above, and the additional material units are preferably of a liquid absorbing skin friendly adhesive material having a lower cohesion, also as described above.

A skin plate product having such a construction and having such material composition is, as mentioned, especially suited for use as semi-manufacture in ostomy equipment or wound dressings, in particular for exudating wounds, since control of the liquid migration in the skin plate product is obtained, and consequently a quick initial liquid absorption as well as a good and longlasting adhesion, as described above.

Figure 2:
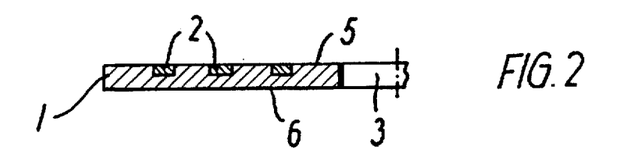
FIGS. 2, 3 and 4 show sections along the line I'—I' of variations of the skin plate product shown in FIG. 1.

FIG. 2 shows a section along the line I—I of the dressing shown in FIG. 1. It appears that the first material unit 1 extends throughout the area of the entire product and constitutes the entire first surface 6 and partly the second surface 5, while the remaining portions of the second surface 5 are constituted by additional material units 2 extending somewhat into the first material unit 1, the three additional material units extending into the same depth and forming an essentially right angle with the surface 5.

Figure 3:
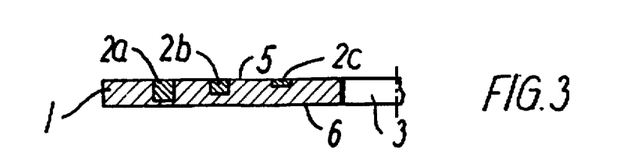
Figure 4:
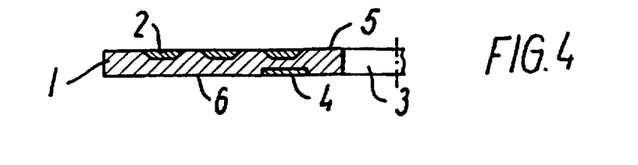

FIGS. 3 and 4 are sections along the line I—I of variations of the skin plate product shown in FIG. 1, the reference numerals 1, 5 and 6 showing corresponding parts as described in FIG. 2.

In FIG. 3 the three additional material units 2 are of different materials, e.g. with variations in cohesion and optionally absorbing capacity, and they extend into different depths.

In FIG. 4 the three additional material units form angles with the surface so as to decrease in width from the surface 5 and into the skin plate product, and further the skin plate product comprises a fourth additional unit which constitutes a surface area of the first surface 6, e.g. in the form of an encircling path area.

This fourth additional unit may e.g. be of a very adhesive and not necessarily skin friendly adhesive material. The unit is intended for being adhered to e.g. an ostomy equipment or a backing layer.

In a variation not shown of the skin plate product shown in FIG. 1, the outermost of the three material units 2 is depressed into the first material unit along the periphery thereof.

Figure 5:
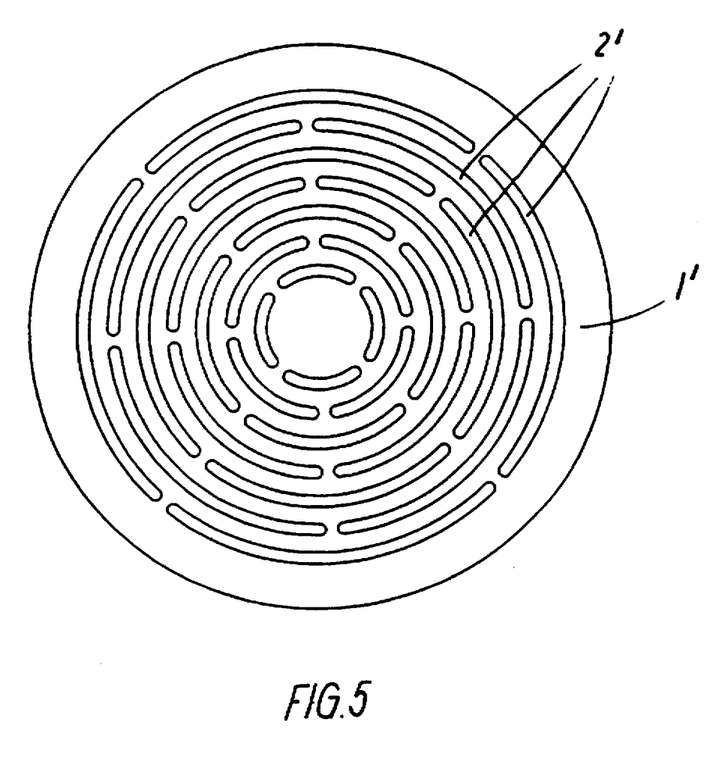
FIG. 5 shows a variation of the embodiment shown in FIG. 1.

The skin plate product shown in FIG. 5 is a variation of the skin plate product shown in FIG. 1, and consists of a first material unit 1' and 28 additional material units 2', and has a first not shown surface and a second surface intended for facing a skin surface.

The second surface is constituted by the first material unit 1' and of the additional material units 2' which are depressed into the first material unit so as to constitute 7 broken path areas of the surface.

The number of path areas can of course be another.

The skin plate product may further have a central aperture (not shown).

The preferred material composition of the material 1' and 2' is as for the corresponding units 1 and 2 in FIG. 1.

The depression depth of the additional material units may vary in the same way as is shown in FIGS. 2–4.

Figure 6:
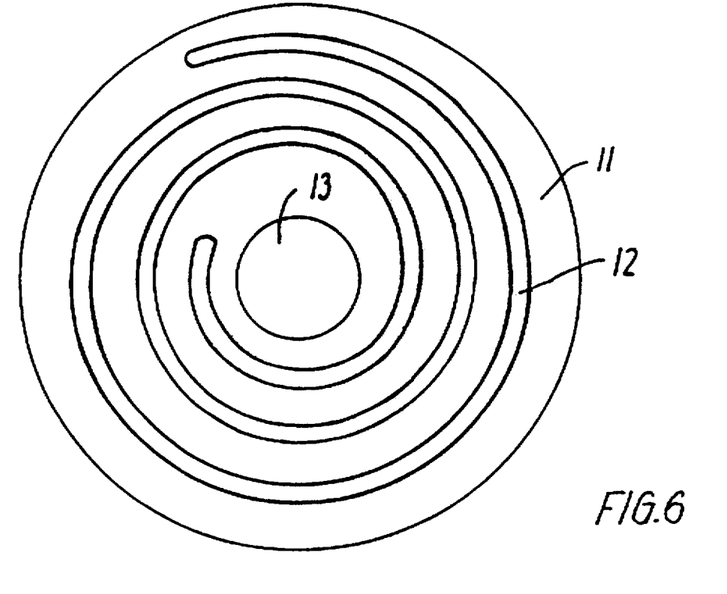
FIG. 6 shows another embodiment of the skin plate product according to the invention seen from the side intended for a skin surface.

The skin plate product shown in FIG. 6 largely corresponds to the skin plate product shown in FIG. 1, as it consists of a first material unit 11 and an additional material unit 12, and has a first (not shown) surface and a second surface being constituted by the two material units, the additional material unit 12 constituting a spiral-shaped area.

The spiral shown in FIG. 6 has three windings, but may of course have more or fewer if desired.

The skin plate product has a central aperture, as it is intended for use in ostomy equipment.

A similar skin plate produce without aperture may e.g. be used as semi-manufacture for a wound dressing.

The preferred material compositions are as stated in the description of FIG. 1.

Figure 7:
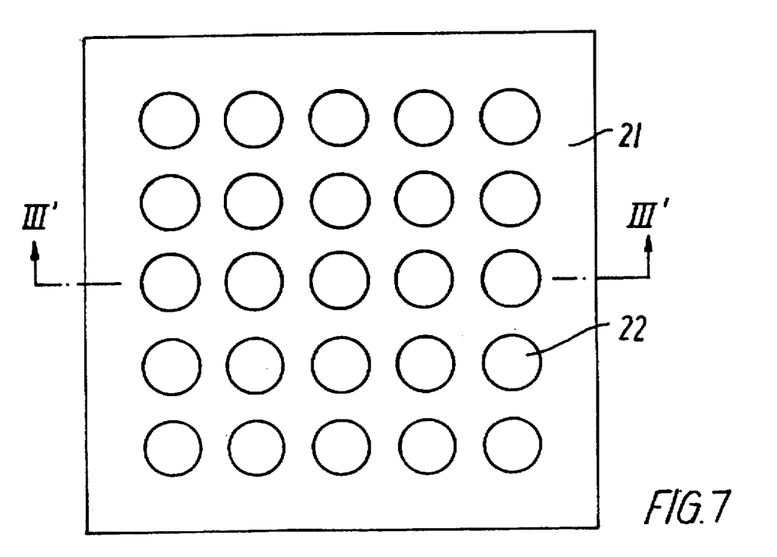
FIG. 7 shows a third embodiment of the skin plate product according to the invention.
Figure 8:
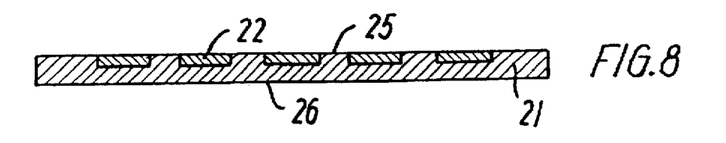
FIG. 8 shows a section along the line III'—III' of the skin plate product shown in FIG. 2.

The skin plate product shown in FIG. 7 and 8 has a first and a second surface 26, 25 and consists of a first material unit 21 and a number of additional material units 22 which constitute a surface area of the second surface 25 in the form of circular islands.

In principle there may be more or fewer islands than shown, and they may optionally be square, oval or have any other shape.

From FIG. 8 it appears that the additional units extend into a depth in the first unit which is the same for all additional units and which is at an essentially right angle with the second surface. It will be understood that the edge surfaces of these units may just as well have another angle in relation to the surface, and that they may extend into different depths.

The first material unit is preferably of a skin friendly self-adhesive material, optionally containing hydrocolloid.

If the skin plate product is to be used as semi-manufacture for a wound or skin care dressing, and the first surface is intended for facing the skin surface, the additional units may e.g. incorporate one or more medicaments as described above and optionally be adhesive and/or liquid absorbing.

If the skin plate product shown in FIG. 7 is to be used as semi-manufacture in an ostomy equipment or as fastening means for wound drains or catheters, it preferably has a material composition as described in FIG. 1.

The skin plate product shown in FIG. 7 may be produced by the method according to the invention by first producing a flat plate of the material which is intended to constitute the first unit 21, e.g. by extrusion. This flat plate may advantageously have a thickness which essentially corresponds to the thickness of the finished product. Thereafter some island-shaped additional units 22 are produced essentially having the shape and thickness which they are intended to have in the finished product.

These additional units are hereafter pressed into the first unit, these additional units advantageously having a lower temperature than the first unit at the moment of pressing in.

Prior to the pressing in of the additional units recesses may e.g. be depressed in the first material unit which correspond to the shape of the additional material units.

Finally, the finished product is punched, the compressed units advantageously being calibrated prior to the punching in order to ensure that the product obtains plane surfaces.

In a variation not shown of the skin plate product shown in FIGS. 7 and 8 the first surface 26 is coated with an additional adhesive layer.

Figures 9, 10:
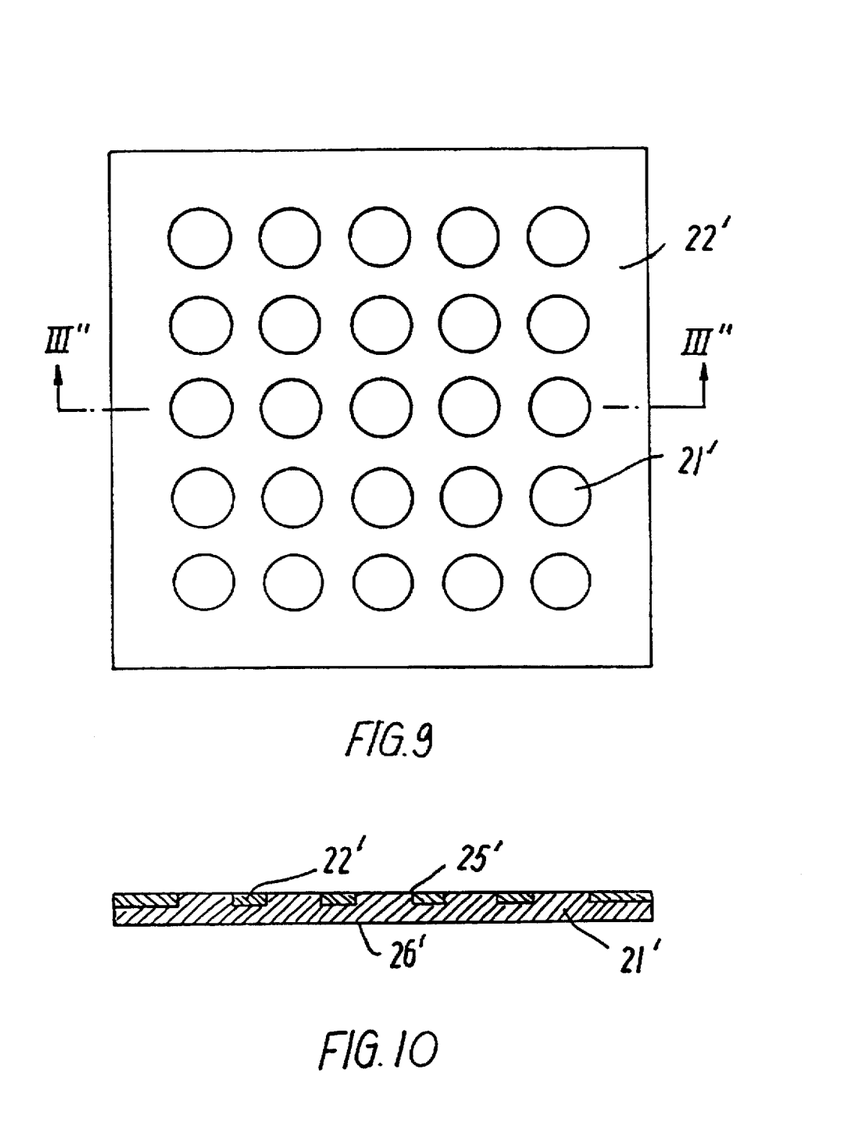
FIG. 9 shows a variation of the embodiment of the skin plate product according to the invention shown in FIG. 7.
FIG. 10 shows a section along the line III"—III" of the skin plate product shown in FIG. 9.

What is shown in FIGS. 9 and 10 is a variation of the skin plate product shown in FIGS. 7 and 8. It consists of a first material unit 21' and an additional material unit 22'. The skin plate product has a first surface 26' being constituted by the first material unit and a second surface 25' being constituted by the additional material unit and a number of islands of the first material unit.

In principle there may be more or fewer islands than shown, and they may optionally be square, oval or have any other shape.

It appears from FIG. 10 that the additional unit extends into a depth in the first unit, which is the same in the entire area of the additional unit, and has an essentially right angle with the second surface. It will be understood that this unit may just as well have another angle in relation to the surface, and that it may extend into varying depths.

Both material units are preferably of skin friendly self-adhesive materials, optionally containing hydrocolloid.

In the embodiment shown in FIGS. 9 and 10 the first material unit may expediently be a hydrocolloid-containing self-adhesive having a relatively low cohesion, and the additional material unit may be a hydrocolloid-containing self-adhesive having a relatively high cohesion.

The embodiment shown in FIG. 9 is produced by the method according to the invention by first producing the plate which is to constitute the first material unit 21' in a thickness which advantageously may be smaller than the thickness which the finished product is intended to have. The additional material unit is advantageously produced by punching, so as to have a periphery which corresponds to the periphery of the finished product and have a number of throughgoing island-shaped apertures.

The additional unit is pressed into the first material unit by methods of pressing in as described in connection with FIG. 7, it having to be ensured that sufficient material is displaced in the first unit for filling out the punched island-shaped apertures in the additional unit. Hereafter the product can be calibrated and punched.

Figure 11:
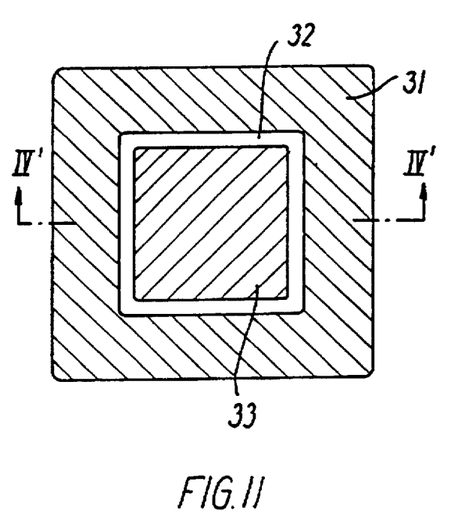
FIG. 11 shows a fourth embodiment of the skin plate product according to the invention seen from the side intended for a skin surface.
Figure 12:
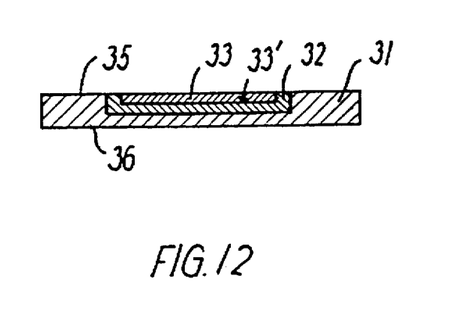
FIG. 12 shows a section along the line IV'—IV' of the skin plate product shown in FIG. 11.

The skin plate product shown in FIGS. 11 and 12 is especially suited as semi-manufacture in a wound or skin plate product, and has a first surface 36 to which a backing layer or the like may be attached, and a second surface 35 intended for facing a skin surface.

The product consists of a first material unit 31 of a skin friendly self-adhesive, liquid absorbing, relatively very cohesive material and a second material unit 32 of a skin friendly self-adhesive, liquid absorbing, less cohesive material, which with the exception of the upper surface encases a third material unit 33 of a material containing a biologically active component. This material may e.g. be of the kind described in Danish patent No. 154 806 and which consists of a continuous water-insoluble phase and a discontinuous phase dispersed therein which is water-soluble or water-swellable, and where the medicament is incorporated in the discontinuous phase. The incorporated medicament will thus be released as liquid dissolves or swells in the discontinuous phase.

The encasing material unit 32 gives the dressing splendid adhesive properties, and the first material unit 31 prevents or reduces liquid seeping in from e.g. catheters and reduces the liquid drainage from the third material unit 33, which entails an almost complete utilization of active substance in the third material unit.

Alternatively, the skin plate product may be constructed without the second material unit, the third material being shapeable and composable according to the wound size and the amount of exudate so as to achieve sufficient adhesive capacity.

The third material unit may alternatively be built from an open-cell foam material containing a medicament or a foam material without medicament.

In an especially preferred embodiment, the third material unit is of an alginate material, e.g. an alginate pad, and optionally without the presence of the second material unit.

As a further alternative, the second material unit which constitutes an encircling area path of the surface may be so shaped that it does not cover the inner surface 33' of the third material unit.

Figure 13:
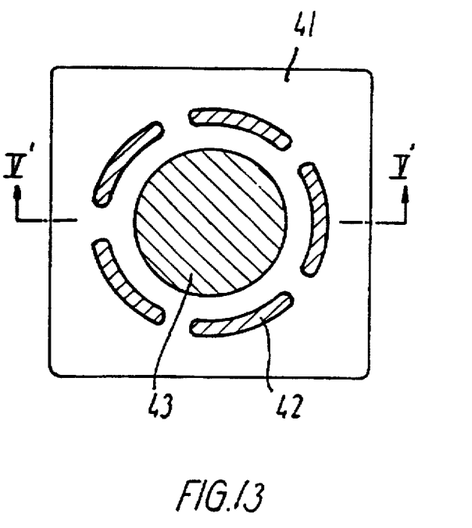
FIG. 13 shows a fifth embodiment of the skin plate product according to the invention seen from the side intended for a skin surface.
Figure 14:
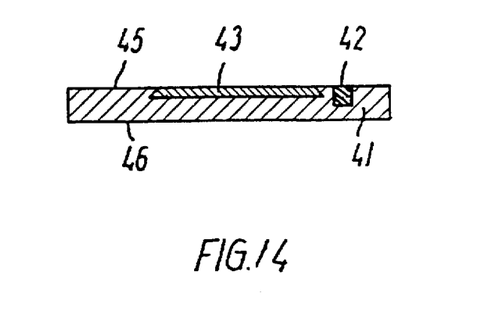
FIG. 14 shows a section along the line V'—V' of the skin plate product shown in FIG. 13.

The skin plate product shown in FIGS. 13 and 14 is also especially suited for use as a semi-manufacture for wound or skin care products, and has a first surface 46 and a second surface 45.

It consists of a first material unit 41, a number of material units 42 and a material unit 43.

The first surface 46 is constituted by the first material unit 41, and the second surface 45 is partly constituted by the first material unit 41, a centrally placed circular island, which might just as well have been square or have another form, of the third material unit and a number of area paths being positioned as a broken circular path constituting the other portions of the second surface.

The broken circular path of the units 42 may of course be shaped as a non-broken path and have any other encircling extension.

Alternatively, the material units 42 may be omitted.

It appears from FIG. 14 that the material unit 43 forms an angle with the surface 45 so as to increase width-wise from the surface 45 and into the material unit 41. To achieve this configuration, it is necessary that the material unit is of an easily deformable material, e.g. a foam material. By a positioning as shown, a better retention of the material unit 43 is obtained.

The materials preferred for the respective units 41, 42 and 43 are the materials described for the units 31, 32 and 33, respectively, in FIG. 1.

What is claimed is:

1. An adhesive, flat skin plate product for use in the production of dressings, skin and wound care devices, adhesive fasteners for dressings, ostomy equipment, breast prostheses, wound drains and catheters for incontinence equipment, and for use in electrodes for application to the skin, said skin plate product comprising:

a first surface and a second surface being planar and substantially parallel;

a thickness defined as the distance between the two surfaces measured in a direction perpendicular to the surfaces; and two or more substantially unmixed material blocks, at least first and second of such two material blocks being of different material and at least one such material block comprising a skin friendly self-adhesive material, wherein the first material block constitutes a portion of the first surface and the entire second surface, and the second material block constitutes the other portion of the first surface, and extends into the thickness of the product in a direction which intersects the first or second surface of the product.

2. An adhesive, flat skin plate product for use in the production of dressings, skin and wound care devices, adhesive fasteners for dressings, ostomy equipment, breast prostheses, wound drains and catheters for incontinence equipment, and for use in electrodes for application to the skin, said skin plate product comprising:

a first surface and a second surface being planar and substantially parallel;

a thickness defined as the distance between the two surfaces measured in a direction perpendicular to the surfaces; and two or more substantially unmixed material blocks, at least first and second of such two material blocks being of different material and at least one such material block comprising a skin friendly self-adhesive material, wherein the first material block constitutes a portion of the first surface and a portion of the second surface, the second material block constitutes the other portion of the first surface, and extends into the thickness of the product in a direction which intersects the first or second surface of the product, and a third material block constitutes the other portion of the second surface, and extends into the thickness of the product in a direction which intersects the first or second surface of the product.

3. A skin plate product according to claim 1, wherein the second material block thickness is less than ¾ of the total thickness of the product.

4. A skin plate product according to claim 1, wherein there are two or more second material blocks and that optionally they have different thicknesses.

5. A skin plate product according to claim 1, wherein at least one second material constitutes a circular or encircling area path of the first or the second surface.

6. A skin plate product according to claim 5, wherein there are at least two concentric circular or encircling area paths constituted by the first material block and that these first material path areas are between 0.3 and 3 times as wide as the most narrow of the area paths of the second material block.

7. A skin plate product according to claim 1, wherein at least one second material block constitutes an island-shaped area of the first or second surface.

8. A skin plate product according to claim 7, wherein it has a centrally positioned island-shaped area section of a second material block, and that optionally it also has on the same surface one or more area paths of second material blocks constituting one or more broken or non-broken circular or encircling area paths positioned around the island-shaped area section.

9. A skin plate product according to claim 1, wherein the first material block constitutes one or more island-shaped area sections of the first or the second surface, or both, and the rest of this or these surfaces are constituted by one or more second material blocks.

10. A skin plate product according to claim 1, wherein the first material block is of a self-adhesive skin friendly material.

11. A skin plate product according to claim 1, wherein at least one of the first and second material blocks is a material reducing or preventing substance migration to and from self-adhesive materials in contact with said at least one of the first and second material blocks.

12. A skin plate product according to claim 11, wherein at least one of the first and second material blocks is a hydrocolloid-containing material hampering or preventing migration of aqueous liquids to hydrocolloid-containing self-adhesive material units in contact therewith.

13. A skin plate product according to claim 12, wherein the first material block is of a skin friendly liquid absorbing adhesive material having a first cohesion, and that at least one second material block is of a skin friendly liquid absorbing adhesive material having a cohesion which is lower than said first cohesion.

14. A skin plate product according to claim 1, wherein at least one of the first and second material blocks contains one or more biologically active substances.

15. A skin plate product according to claim 14, wherein at least one of the first and second material blocks comprises a hydrophilic gel material incorporating an agent effective against warts, or incorporating one or more mitosis impeding compounds.

16. A skin plate product according to claim 1, wherein at least one of the first and second material blocks is an alginate material.

17. A skin product according to claim 1, wherein the second material block has a thickness of less than ½ of the total thickness of the product and the thickness of the second material block is 0.1–3 mm.

18. A skin plate product according to claim 17, wherein the second material block has a thickness of 0.5–1.5 mm.

19. A skin plate product according to claim 5, wherein there are at least two circular or encircling area paths positioned concentrically.

20. A skin plate product according to claim 5, wherein the circular or encircling broken path area is discontinuous.

* * * * *